US005465145A

United States Patent [19]
Nakashige et al.

[11] Patent Number: 5,465,145
[45] Date of Patent: Nov. 7, 1995

[54] SEMICONDUCTOR WAFER INSPECTION APPARATUS

[75] Inventors: Yukiko Nakashige; Tadashi Nishioka, both of Hyogo, Japan

[73] Assignees: Mitsubishi Denki Kabushiki Kaisha, Tokyo; Ryoden Semiconductor System Engineering Corporation, Hyogo, both of Japan

[21] Appl. No.: 309,999

[22] Filed: Sep. 20, 1994

[30] Foreign Application Priority Data

Oct. 18, 1993 [JP] Japan .................................. 5-260201

[51] Int. Cl.⁶ ................................................ G01N 21/88
[52] U.S. Cl. .......................................... 356/237; 359/884
[58] Field of Search ................................ 356/237, 336; 359/839, 884

[56] References Cited

U.S. PATENT DOCUMENTS 4,601,576  7/1986  Galbraith .............................. 356/237

FOREIGN PATENT DOCUMENTS 4-170543  6/1992  Japan .
4-305951  10/1992  Japan .

OTHER PUBLICATIONS

"Comparison of Two Wafer Inspection Methods for Particle Monitoring in Semiconductor Manufacturing", Leon Pesotchinsky et al., IEEE Transactions on Semiconductor Manufacturing, vol. 1, No. 1, Feb. 1988, pp. 16–22.
"Particle–Free Wafer Cleaning and Drying Technology", H. Mishima et al., IEEE Transactions on Semiconductor Manufacturing, vol. 2., No. 3 Aug. 1989, pp. 69–75.
"Particle Deposition and Removal in Wet Cleaning Processes for ULSI Manufacturing", Mitsushi Itano et al., IEEE Transactions on Semiconductor Manufacturing, vol. 5, No. 2, May 1992, pp. 114–120.

*Primary Examiner*—Vincent P. McGraw
*Attorney, Agent, or Firm*—Lowe, Price, LeBlanc & Becker

[57] ABSTRACT

Disclosed is a semiconductor wafer inspection apparatus which effectively prevents an erroneous identification of small pits as particles on a surface of a sample. In such a semiconductor wafer inspection apparatus, a light collecting portion and a reflection adjustment portion having a light reflectance different from a light reflectance of the light collecting portion are included in light collecting means.

11 Claims, 14 Drawing Sheets

INTENSITY OF
SCATTERED LIGHT [log( I / Io )]

ANGLES OF
SCATTERED LIGHT [ θ ]

SEMICONDUCTOR WAFER INSPECTION APPARATUS

BACKGROUND OF THE INVENTION

1. Field of the Invention

The present invention relates to semiconductor wafer inspection apparatuses, and more particularly, to a semiconductor wafer inspection apparatus for measuring diameters of particles and counting those particles on a surface of a semiconductor wafer.

2. Description of the Background Art

Conventionally, a semiconductor wafer inspection apparatus has been known that is used for measuring diameter of particles and counting those particles on a surface of a semiconductor wafer according to a distribution of intensity of scattered light with respect to angles of scattering, using the Layleigh-Debye approximation or the like. Such an apparatus is disclosed, for example, in Leon L. Pesotchinsky and Zinovy Fichtenholz: *IEEE Transactions Semiconductor Manufacturing*, Vol. 1, No. 1, pp. 16–22, 1988.

FIG. 17 is a schematic diagram showing a structure of a conventional semiconductor wafer inspection apparatus. Referring to FIG. 17, in the conventional semiconductor wafer inspection apparatus 700, there is provided a sample placing portion 200 having a stage 220 for scanning a sample (semiconductor wafer) 210 two dimensionally. Also provided is a light projecting portion 100 for generating a beam of light 110 with which a surface of sample 210 is irradiated. A light collecting portion 300 is provided between light projecting portion 100 and sample placing portion 200 for collecting light scattered from the surface of sample 210. Light collecting portion 300 includes a ellipsoid of revolution. A light receiving portion 500 is provided at the focus (F2) of scattered light collected by light collecting portion 300 for measuring a total amount of collected light. Also provided is a measurement control portion 600 for driving light projecting portion 100 and sample placing portion 200 and for processing an output signal supplied from light receiving portion 500.

As for an operation of the conventional semiconductor wafer inspection apparatus 700, firstly, measurement control portion 600 transmits a drive signal to light projecting portion 100 for generating a beam of light 110 from light projecting portion 100. Beam of light 110 passes through an optical beam inlet hole 310 provided at light collecting portion 300 to become an incident light 120. A particle 230 on the surface of sample 210 is irradiated with incident light 120. A point where incident light 120 crosses sample 210 is the focus (F1) of light collecting portion 300. Beams of light scattered by irradiation of particle 230 with incident light 120 are collected to the other focus (F2) by light collecting portion 300. The scattered light collected to the focus (F2) is received by light receiving portion 500, whereby an intensity of scattered light corresponding to particle 230 is measured. Accordingly, a diameter of particle 230 can be measured. The above operation is carried out with stage 220 moved so that measurement and counting of particles 230 on the surface of sample 210 can be carried out.

However, there has been an inconvenience in the above conventional semiconductor wafer inspection apparatus 700 such that a very small pit (hole) on the surface of sample 210 could be identified as a particle by mistake. FIG. 18 is a schematic diagram showing scattering of light caused by a very small pit on the surface of sample 210. FIG. 19 is a graph showing a distribution of intensity of scattered light with respect to angles of scattering in the case when the particle exists on the surface of the sample (P), when a pit exists on the surface of the sample (S), and when neither the particle nor the pit exists on the surface of the sample (N).

Referring to FIG. 19, it is assumed that an intensity of scattered light at a scattering angle $\theta=0$ is $I_0$, and that an intensity of scattered light at the other angles $\theta$ is I. A normalized log $(I/I_0)$ is plotted corresponding to a light scattering angle $\theta$. As shown in FIG. 19, in the range of $0-\theta_s$ where light scattering angles are small, almost the same distribution of intensity of scattered light with respect to angles of light scattering is obtained when the particle exists (P) and when the pit exists (S) on the surface of sample 210. In such a range of light scattering angles $0-\theta_s$, the intensity of scattered light is very much greater than that at larger angles of scattering. In this respect, as shown in FIG. 19, even when there is an apparent difference between (P) and (S) at larger angles of light scattering, ratio of a total amount of scattered light of (P) to that of (S) becomes smaller if the difference between (P) and (S) is negligible in the range of smaller angles $(0-\theta_s)$ of light scattering.

Therefore, it has been difficult to clearly distinguish the scattered light (S) caused by pit 240 from the scattered light (P) caused by particles when measuring the total amount of scattered light (S) when the small pit 240 exists (see FIG. 18) and the total amount of scattered light (P) when particles 230 exist (see FIG. 17) on the surface of sample 210. Accordingly, the scattered light (S) caused by pit 240 could erroneously be identified as scattered light (P) caused by particles. Correct measurement of diameters of particles on the surface of sample 210 and counting the number of those particles have been difficult with the conventional semiconductor wafer inspection apparatus 700.

SUMMARY OF THE INVENTION

An object of the present invention is to correctly measure diameters and count the number of particles on a surface of a semiconductor wafer in a semiconductor wafer inspection apparatus.

Another object of the present invention is to clearly distinguish scattered light caused by particles from scattered light caused by pits in a semiconductor wafer inspection apparatus.

In one aspect of the present invention, a semiconductor wafer inspection apparatus includes a light projecting means, a light collecting means, and a light receiving means. The light projecting means is provided for directing a beam of light onto a main surface of the semiconductor of wafer. The light collecting means is provided for collecting beams of light scattered from the main surface of the semiconductor wafer. The light receiving means is provided for receiving scattered light collected by the light collecting means and measuring intensity of scattered light. The light collecting means includes a light collecting portion having a first light reflectance and a reflection adjustment portion having a second light reflectance different from the first light reflectance.

In such a semiconductor wafer inspection apparatus, since the light collecting means includes the light collecting portion having the first light reflectance and the reflection adjustment portion having the second light reflectance different from the first light reflectance, when, for example, the second light reflectance is made smaller than the first light reflectance, intensity of scattered light emitted from the reflection adjustment portion is made smaller than intensity of scattered light emitted from the light collecting portion even if intensity of scattered light incident on the light collecting portion is equal to intensity of scattered light incident on the reflection adjustment portion. If such a reflection adjustment portion is provided within the scattering angle range where there is the same distribution of intensity of scattered light with respect to angles of light scattering when particles exist on the surface of the sample and when pits exist, the intensity of scattered light within such a range of scattering angle would be weaker than in other ranges. This contributes to relative increase of the intensity of scattered light within the scattering angle range where a difference between the intensity of scattered light caused by particles and that caused by pits is conspicuous. Accordingly, when the total amount of scattered light caused by particles and that caused by pits are measured by the light receiving means, ratio of the total amount of scattered light caused by particles to that caused by pits becomes greater than before. The scattered light caused by pits and the scattered light caused by particles are thus distinguished from each other easily and clearly. This eliminates an inconvenience of erroneous identification of the scattered light caused by pits as the scattered light caused by particles. Since the intensity of scattered light is held at a certain level even in the scattering angle range where the intensity of scattered light is reduced by the reflection adjustment portion, it is easy to determine whether or not particles exist. As a result, diameters and the number of particles on the surface of the sample can be correctly detected. Also, if the second light reflectance is made greater than the first light reflectance, and if the reflection adjustment portion is provided within the scattering angle range where the intensity of scattered light is great, anything abnormal on the surface of the sample can be detected with high sensitivity. If the reflection adjustment portion is provided to include a first reflection adjustment portion having a third light reflectance and a second reflection adjustment portion having a fourth light reflectance different from the third light reflectance, a distribution of intensity of scattered light reflected on the reflection adjustment portion can be adjusted more properly. If the reflection adjustment portion is provided to include a liquid crystal having a dynamic scattering mode, the reflectance of the reflection adjustment portion can be easily changed by altering a voltage value applied to the liquid crystal.

In another aspect of the present invention, a semiconductor wafer inspection apparatus includes a light projecting means, a light collecting means, a light receiving means, a reference light detecting means, and a light reflectance control means. The light collecting means is provided for collecting beams of light scattered from a main surface of a semiconductor wafer and includes a light collecting portion having a first light reflectance and a reflection adjustment portion made of a liquid crystal having a second light reflectance different from the first light reflectance. The reference light detecting means is provided for detecting reference light transmitted through the liquid crystal of the reflection adjustment portion. The light reflectance control means is provided for controlling a light reflectance of the reflection adjustment portion according to a detection output of the reference light detecting means.

In such a semiconductor wafer inspection apparatus, the reflection adjustment portion made of liquid crystal and having the second light reflectance is included in the light collecting portion, the reference light transmitted through the liquid crystal of the reflection adjustment portion is detected by the reference light detecting means, and the light reflectance of the reflection adjustment portion is controlled by the light reflectance control means according to the detection output of a reference light detecting means. Thus, the dynamic scattering mode of the liquid crystal can be easily controlled in a feedback loop by the reference light reflecting the reflectance of the reflection adjustment portion. As a result, the light reflectance of the reflection adjustment portion can be controlled more correctly.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Description will be given below for embodiments of the present invention in conjunction with the drawings.

Figure 1:
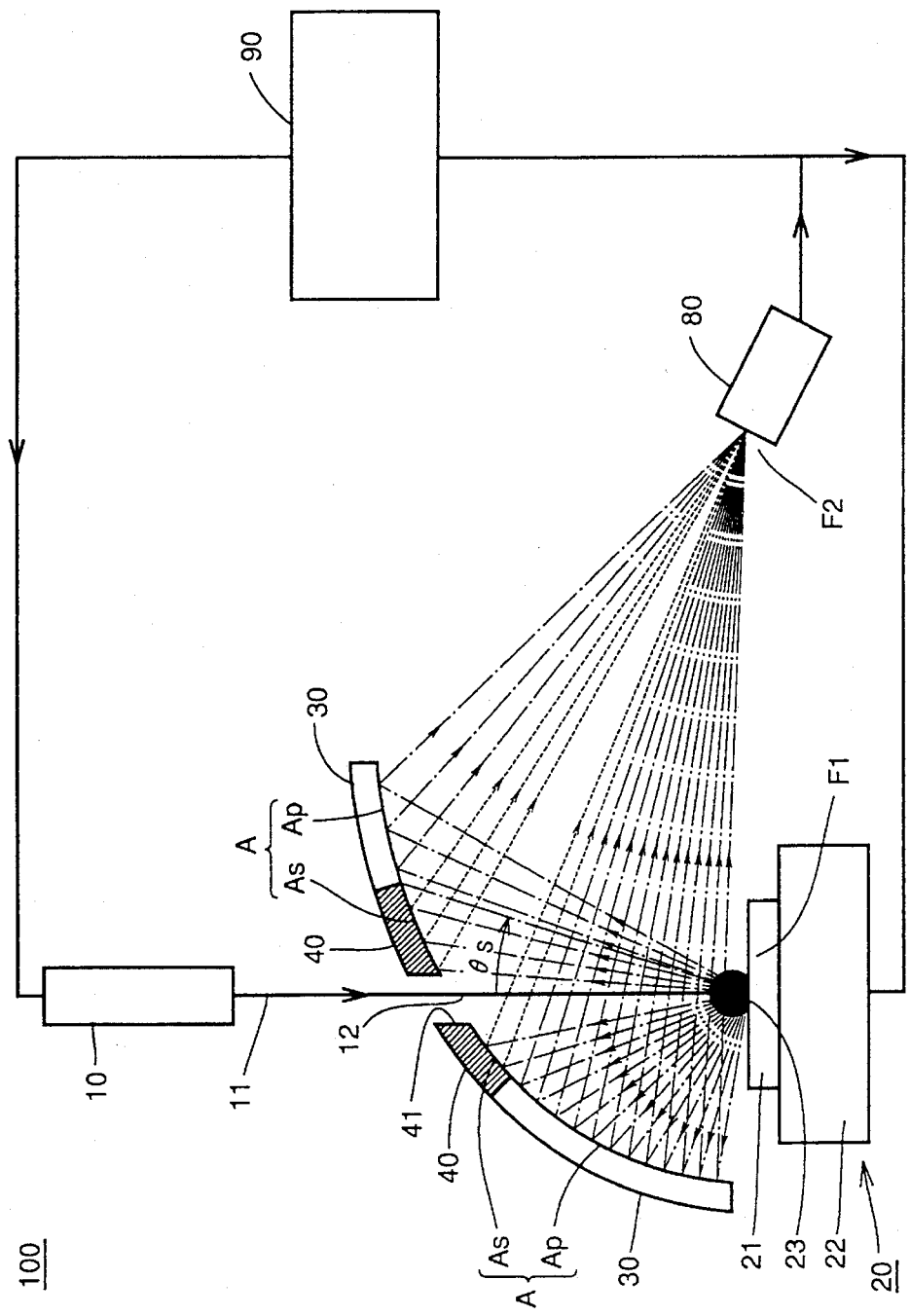
FIG. 1 is a schematic diagram showing a structure of a semiconductor wafer inspection apparatus according to a first embodiment of the present invention.

Referring to FIG. 1, in a semiconductor wafer inspection apparatus 100 according to a first embodiment, a sample placing portion 20 including a stage 22 is provided for scanning a sample (semiconductor wafer) 21 two dimensionally. A light projecting portion 10 for generating a beam of light 11 with which a surface of sample 21 is irradiated is also provided. A light collecting portion 30 and a reflection adjustment portion 40 formed continuously with light collecting portion 30 are provided between light projecting portion 10 and sample placing portion 20.

Light collecting portion 30 and reflection adjustment portion 40 are constituted by a portion of a ellipsoid of revolution having two focus of F1 and F2. Light collecting portion 30 has a mirror surface $A_p$, and reflection adjustment portion 40 has a mirror surface $A_s$. Mirror surface $A_p$ and mirror surface $A_s$ form a mirror surface A. An optical beam inlet hole 41 is provided in reflection adjustment portion 40 for passing beam of light 11 therethrough. Reflection adjustment portion 40 has a circular shape in a planar layout. Radius of the circle is a distance from optical beam inlet hole 41 to focus F1 multiplied by $\tan\theta_s$. Reflection adjustment portion 40 is thus structured so that the light scattered within a certain range of angles ($0-\theta_s$) are incident on reflection adjustment portion 40. A reflectance of mirror surface $A_s$ of reflection adjustment portion 40 is set to 1/10 of a reflectance of mirror surface $A_p$ of light collecting portion 30, for example.

A light receiving portion 80 is provided for measuring intensity of scattered light at focus F2 where scattered light reflected from light collecting portion 30 and reflection adjustment portion 40 are collected. Light projecting portion 10, sample placing portion 20, and light receiving portion 80 connect to a measurement control portion 90. Measurement control portion 90 controls driving of light projecting portion 10 and sample placing portion 20 and processes an output signal supplied from light receiving portion 80. More particularly, measurement control portion 90 controls operation and adjustment of beam of light 11 and controls scanning operation of stage 22. Measurement control portion 90 also controls operation of light receiving portion 80 and analyzes input/output signals supplied from light receiving portion 80 to calculate diameters and the number of particle 23. Measurement control portion 90 can display the result of calculation.

Now, in semiconductor wafer inspection apparatus 100 according to the first embodiment, the reflectance of mirror surface $A_s$ of reflection adjustment portion 40 is set to 1/10 of the reflectance of mirror surface $A_p$ of light collecting portion 30, as described earlier. Thus, even if the intensity of scattered light incident on reflection adjustment portion 40 is equal to that incident on light collecting portion 30, the intensity of scattered light emitted from reflection adjustment portion 40 is 1/10 of the intensity of scattered light emitted from light collecting portion 30. In this respect, when the total amount of scattered light is measured by light receiving portion 80, the distribution of intensity of scattered light reflected from light collecting portion 30 is emphasized compared with that reflected from reflection adjustment portion 40.

Figure 2:
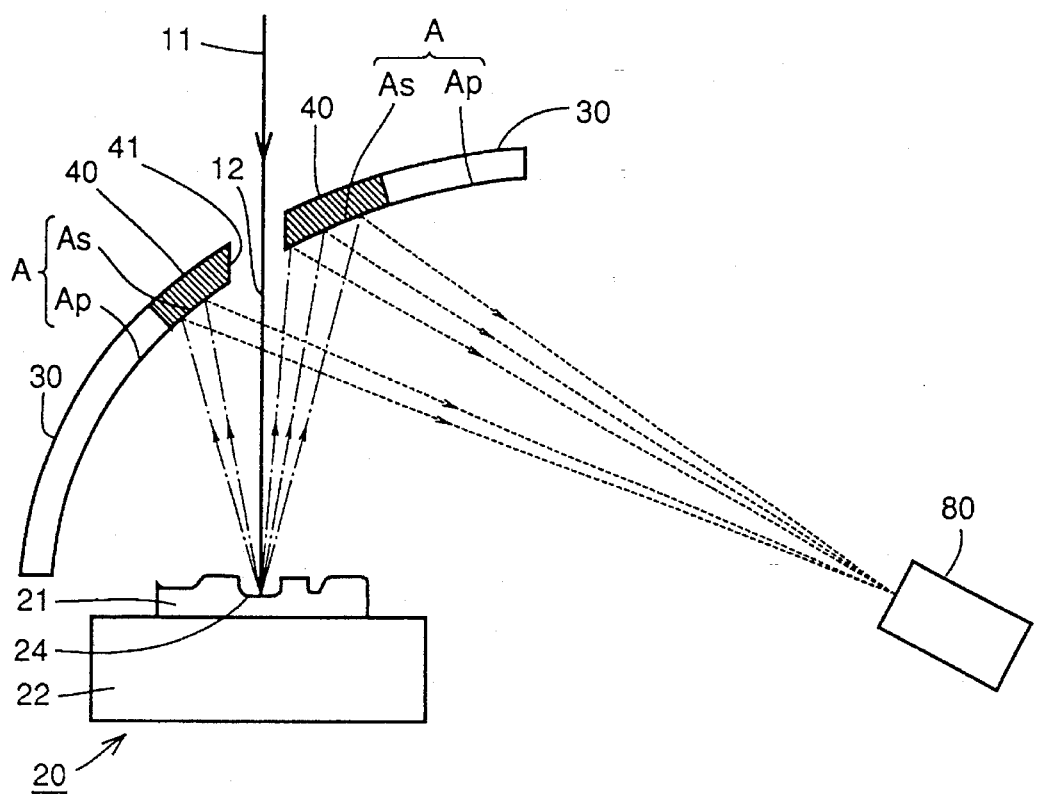
FIG. 2 is a schematic diagram showing scattering light when pits on a surface of a sample are detected by the semiconductor wafer inspection apparatus according to the first embodiment shown in FIG. 1.

FIG. 2 is a schematic diagram illustrating a distribution of intensity of scattered light when a pit 24 exists on sample (semiconductor wafer) 21.

Figure 3:
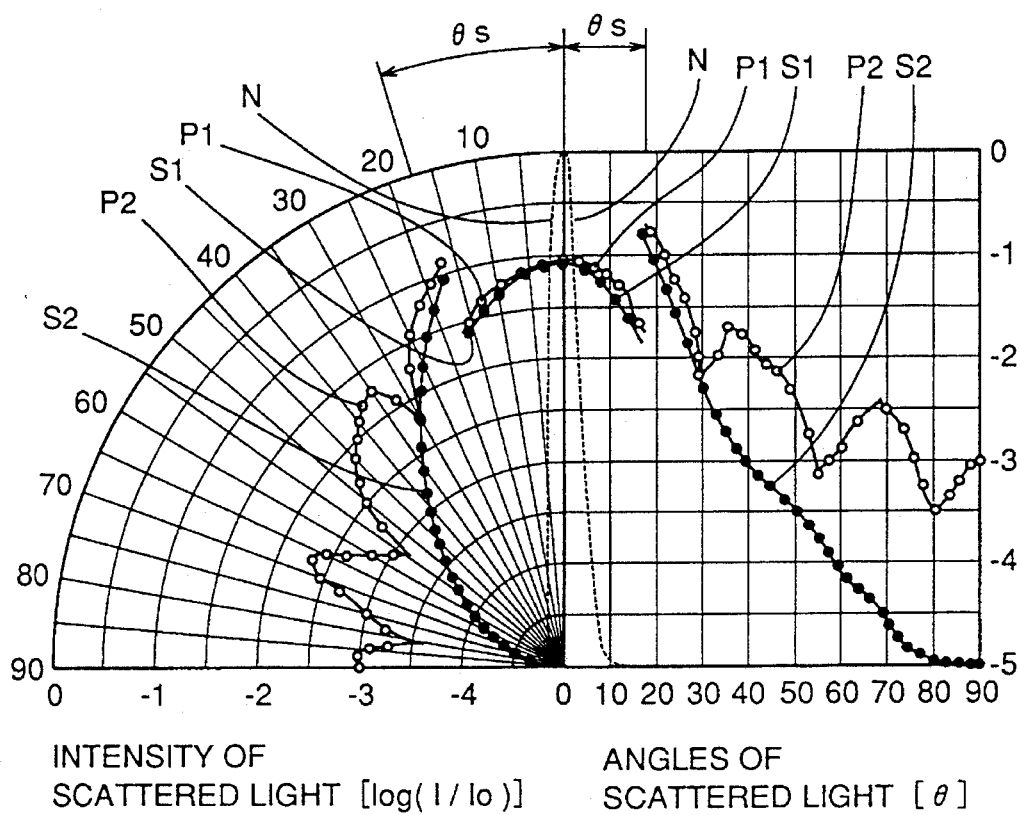
FIG. 3 is a graph showing measurement results of intensity of scattered light in the cases of the presence of pits, the presence of particles, and the absence of particles and the pits on the surface of the sample, using the semiconductor wafer inspection apparatus according to the first embodiment as shown in FIG. 1.

Referring to FIGS. 1–3, intensity of scattered light at a scattering angle of $\theta=0$ is represented by $I_0$, and intensity of scattered light at the other scattering angles is represented by I, and the normalized log ($I/I_0$) is plotted. It is noted that intensity of scattered light (log ($I/I_0$)) is smaller in the range of scattering angles of $0-\theta_s$ corresponding to reflection adjustment portion 40 than in the range of scattering angles of $\theta_s$ or more (see FIG. 3). This is because the light reflectance of reflection adjustment portion 40 has been set to 1/10 of the light reflectance of light collecting portion 30.

With such a structure, intensity of scattered light within the range of scattering angles $0-\theta_s$, where the intensity of scattered light caused by particle (P1) is almost equal to the intensity of scattered light caused by pit (S1), can be made smaller than the intensity of scattered light within the other range of scattering angles of $\theta_s$ or more. Accordingly, the intensity of scattered light within the range of scattering angles of $\theta_s$ or more where the difference between the intensity of scattered light caused by particle (P2) and the intensity of scattered light caused by pit (S2) is apparent can be increased relatively. As a result, when the total amount of scattered light caused by particle (P1, P2) and that caused by pit (S1, S2) are measured by light receiving portion 80, the ratio of the total amount of scattered light caused by particles to that caused by pits is made greater than before.

The scattered light caused by pits and the scattered light caused by particles can thus be distinguished from each other clearly. This can prevents effectively an erroneous identification of the scattered light caused by pits as the scattered light caused by particles as before. This also improves an accuracy of measurement of diameters and the number of particles than before. Although the intensity I of scattered light within the range of scattering angles of $0-\theta_s$ is reduced to 1/10 of the intensity at the other angles, such a reduced intensity is sufficient to detect the presence of particle 23 on the surface of sample 21.

Figure 4:
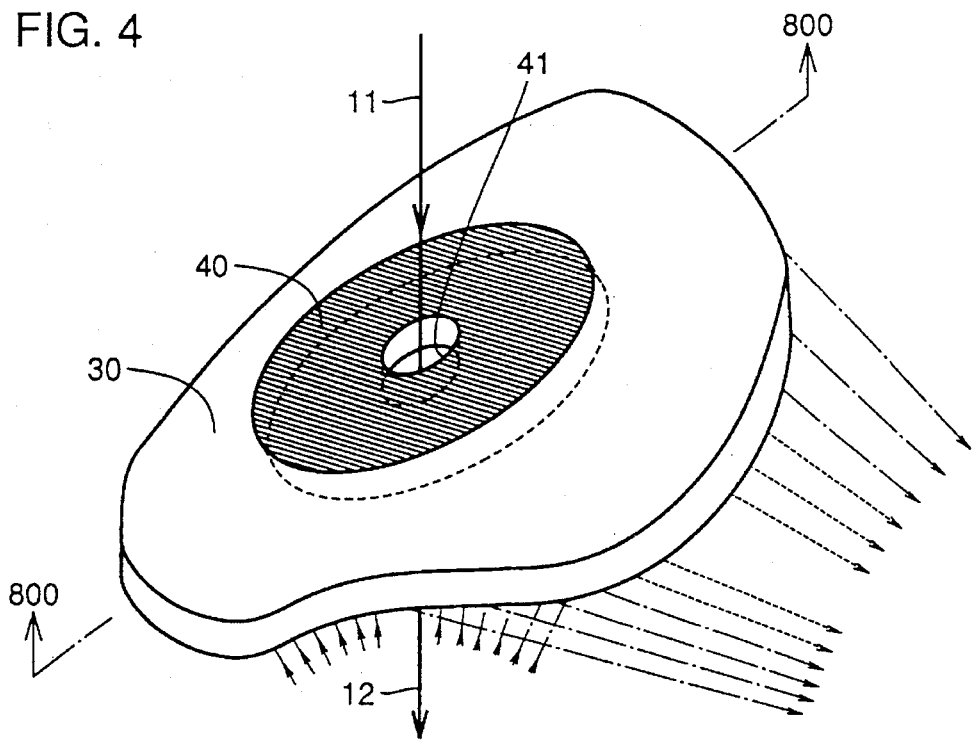
FIG. 4 is a oblique projection view showing a light collecting portion and a reflection adjustment portion of the semiconductor wafer inspection apparatus according to the first embodiment shown in FIG. 1.
Figure 5:
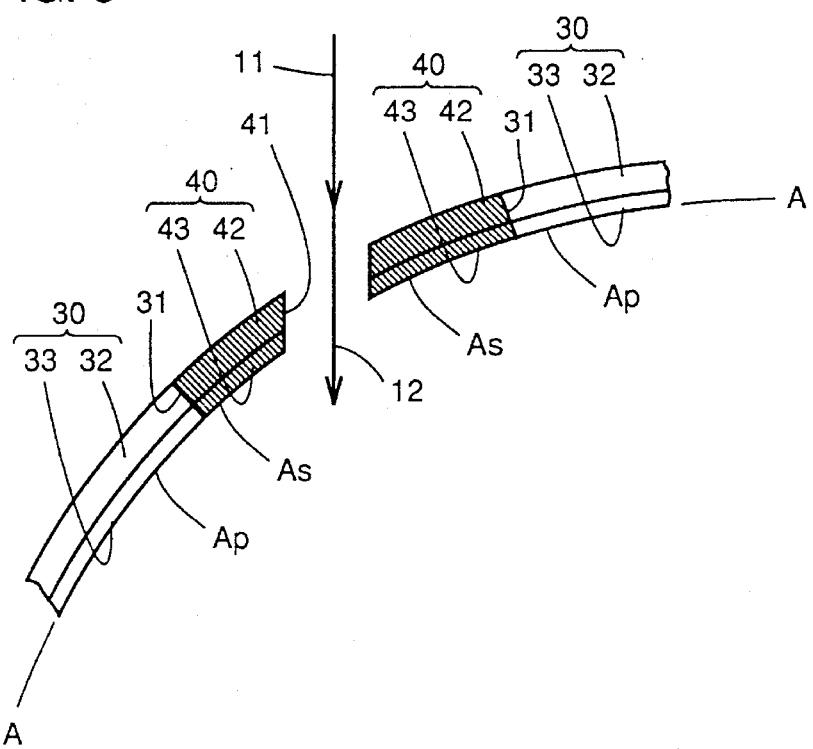
FIG. 5 is a sectional view taken of the reflection adjustment portion and the light collecting portion taken along line 800—800 shown in FIG. 4.

Referring to FIGS. 4 and 5, description will be made on a structure of light collecting portion 30 and reflection adjustment portion 40 of the semiconductor wafer inspection apparatus according to the first embodiment in greater detail.

Light collecting portion 30 is formed by a base material 32 of the light collecting portion having mirror surface $A_p$ of a ellipsoid of revolution, and a light collecting film 33 having a large reflectance and formed on mirror surface $A_p$ of base material 32 of the light collecting portion. Reflection adjustment portion 40 is formed by a base material 42 of the reflection adjustment portion having mirror surface $A_s$ continuous with mirror surface $A_p$, and a reflection adjustment film 43 having a reflectance smaller than that of light collecting film 33 and formed on mirror surface $A_s$ of base material 42 of the reflection adjustment portion.

Base material 32 of the light collecting portion is made by, for example, plastic forming (press molding) of a stainless steel plate or an aluminum alloy plate. The base material 32 of the light collecting portion may be formed by injection molding of a plastic material. An arrangement of sample placing portion 20 (see FIG. 1), a light path of scattered light, and light receiving portion 80 should be taken into consideration when base material 32 of the light collecting portion is formed. Base material 32 of the light collection portion has a hole portion 31 having a predetermined radius with beam of light 11 being a central axis, when viewed as a plane.

Light collecting film 33 is made of a film having a large spectral reflectance with respect to a wavelength of beam of light 11, or a dielectric multi-layer film. In other words, light collecting film 33 is obtained by quick evaporation of aluminum, silver or the like in high vacuum on mirror surface $A_p$ of base material 32 of the light collecting portion.

Base material 42 of the reflection adjustment portion has an external diameter slightly smaller than the diameter of hole portion 31 provided in light collecting portion 30. Base material 42 of the reflection adjustment portion also has optical beam inlet hole 41 which is coaxially provided with hole portion 31. Base material 42 of the reflection adjustment portion is made of a transparent, semi-transparent or opaque organic glass, or inorganic glass or metal.

Reflection adjustment film 43 is made of such a dielectric multi-layer film that has spectral reflectance of ⅒ of the spectral reflectance of light collecting film 33 with respect to the wavelength of beam of light 11. On the surface of light collecting film 33 and reflection adjustment film 43, a thin film of magnesium fluoride may be provided for improving endurance of those films. Base material 42 of reflection adjustment portion 42 is bonded to hole portion 31 of base material 32 of the light collecting portion with an epoxy resin or the like.

Light receiving portion 80 (see FIG. 1) is formed by an optical fiber cable (not shown) having one end placed at focus F2, and a light detector (not shown) connected to the other end of the optical fiber cable. For example, such a photomultiplier that has the spectral sensitivity characteristic which can cover the wavelength of incident light 12 is used as the light detector. Light collecting portion 80 includes an electronic circuit allowing adjustment of output gains by changing voltages applied to the photomultiplier (the light detector).

A laser light source and an optical system are incorporated in light projecting portion 10 (see FIG. 1). As the laser light source, ArII gas laser having a wavelength of 488 nm is used, for instance. The optical system consists of such lenses that have the diameter of about 45 μm of incident light 12 with which sample 21 is irradiated.

Measurement control portion 90 (see FIG. 1) can control the operation of the laser light source constituting light projecting portion 10 and controls output of incident light 12.

Sample placing portion 20 (see FIG. 1) has an attach/detach mechanism of sample (semiconductor wafer) 21. An X-Y stage using a stepping motor or any stage allowing scanning of X-axis and rotating of the sample is used as stage 22. Measurement control portion 90 instructs the operation of stage 22 or changes the scanning speed of the X-Y stage or the rotating speed of the rotating stage.

Figure 6:
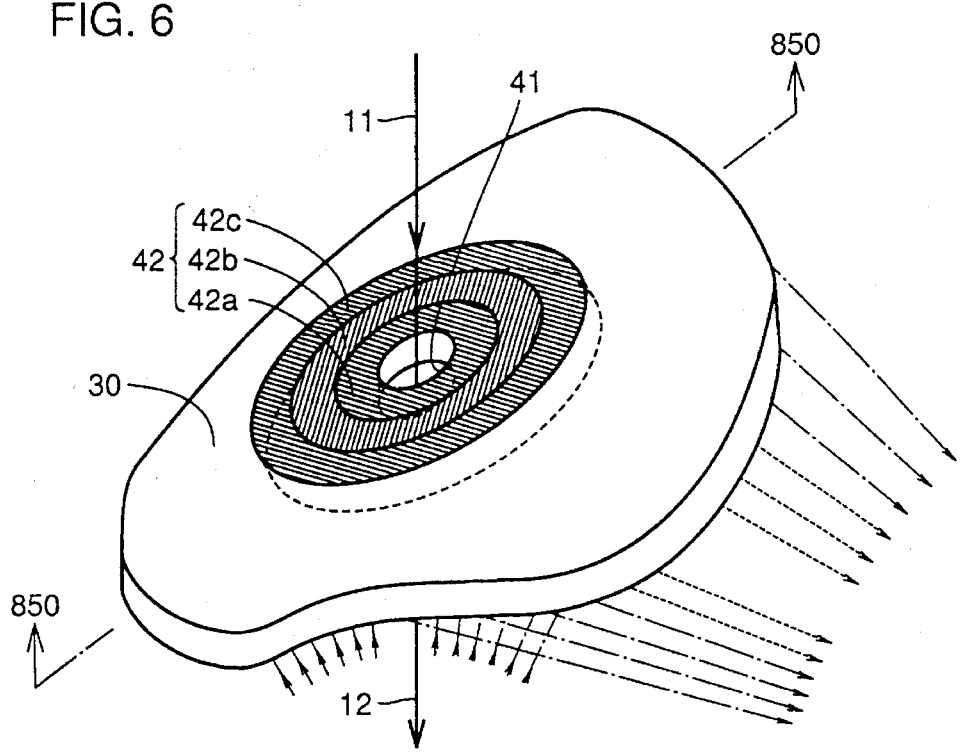
FIG. 6 is a oblique projection view showing a light collecting portion and a reflection adjustment portion of a semiconductor wafer inspection apparatus according to a second embodiment of the present invention.
Figure 7:
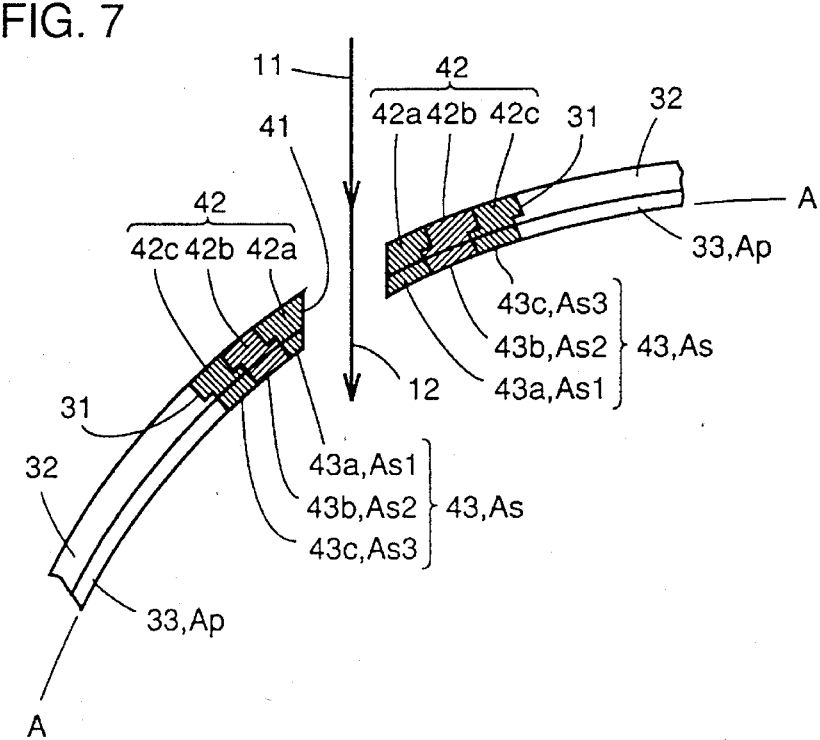
FIG. 7 is a sectional view of the light collecting portion and the reflection adjustment portion taken along line 850—850 shown in FIG. 6.

Referring to FIGS. 6 and 7, it is noted that in the second embodiment the reflection adjustment portion consists of the first through third reflection adjustment portions each having a different reflectance. More particularly, the first reflection adjustment portion is formed of a first base material 42a of the reflection adjustment portion and a first reflection adjustment film 43a. The second reflection adjustment portion is formed of a second base material 42b of the reflection adjustment portion and a second reflection adjustment film 43b. The third reflection adjustment portion is formed of a third base material 42c of the reflection adjustment portion and a third reflection adjustment film 43c. Optical beam inlet hole 41 light is provided in first base material 42a of the reflection adjustment portion.

Third base material 42c of the reflection adjustment portion is fitted in hole portion 31 of base material 32 of the light collecting portion. Second base material 42b is fitted in an internal hole of third base material 42c, and first base material 42a is fitted in an internal hole of second base material 42b. A stepped portion is provided at hole 31, the internal hole of third base material 42c, the internal hole of second base material 42b, the outer peripheral portion of third base material 42c, the outer peripheral portion of second base material 42b, and the outer peripheral portion of first base material 42a, respectively. First through third base materials 42a, 42b, and 42c of the reflection adjustment portion can therefore be assembled easily with such stepped portions.

Figure 8:
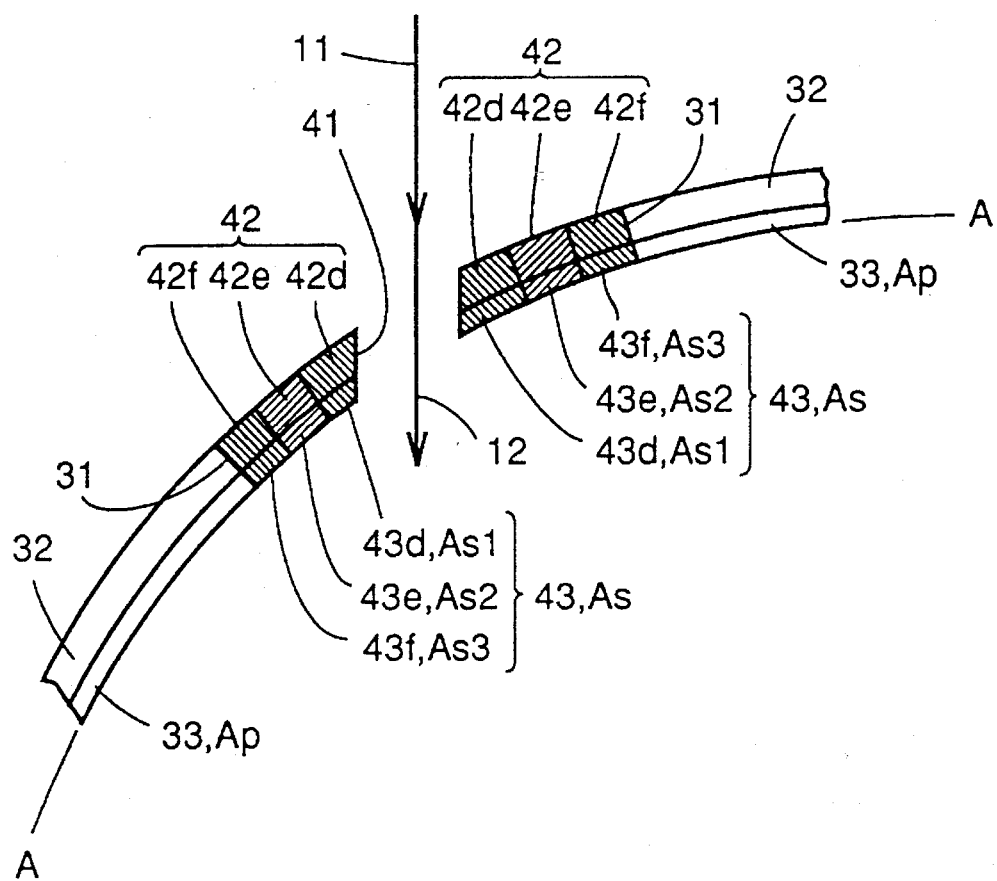
FIG. 8 is a sectional view showing a modified example of the reflection adjustment portion according to the second embodiment shown in FIG. 7.

It is noted in a modified example shown in FIG. 8 that stepped portions may not be provided at a first base material 42d of the reflection adjustment portion, a second base material 42e, and a third base material 42f. In this case, an adhesive such as epoxy resin is applied to bond base material 32 of the light collecting portion to third base material 42f, third base material 42f to second base material 42e, and second base material 42e to first base material 42b. First reflection adjustment film 43d, second reflection adjustment film 43e and third reflection adjustment film 43f are respectively provided on the surfaces of first base material 42d, second base material 43e, and third base material 42f.

The widths of first reflection adjustment films 43a, 43d, second films 43b, 43e, and third films 43c, 43f correspond to $\theta_s/3$ of the scattering angle $\theta_s$ shown in FIG. 1. Reflectance of mirror surface $A_s1$, $A_s2$, $A_s3$ are ⅒, ⅕, and ½ of the reflectance of mirror surface $A_p$, respectively. In order to change the reflectance of mirror surface $A_s1$, $A_s2$, $A_s3$ as above, the dielectric multi-layer film, for example, is used as first through third reflection adjustment films 43a–43f.

Figure 9:
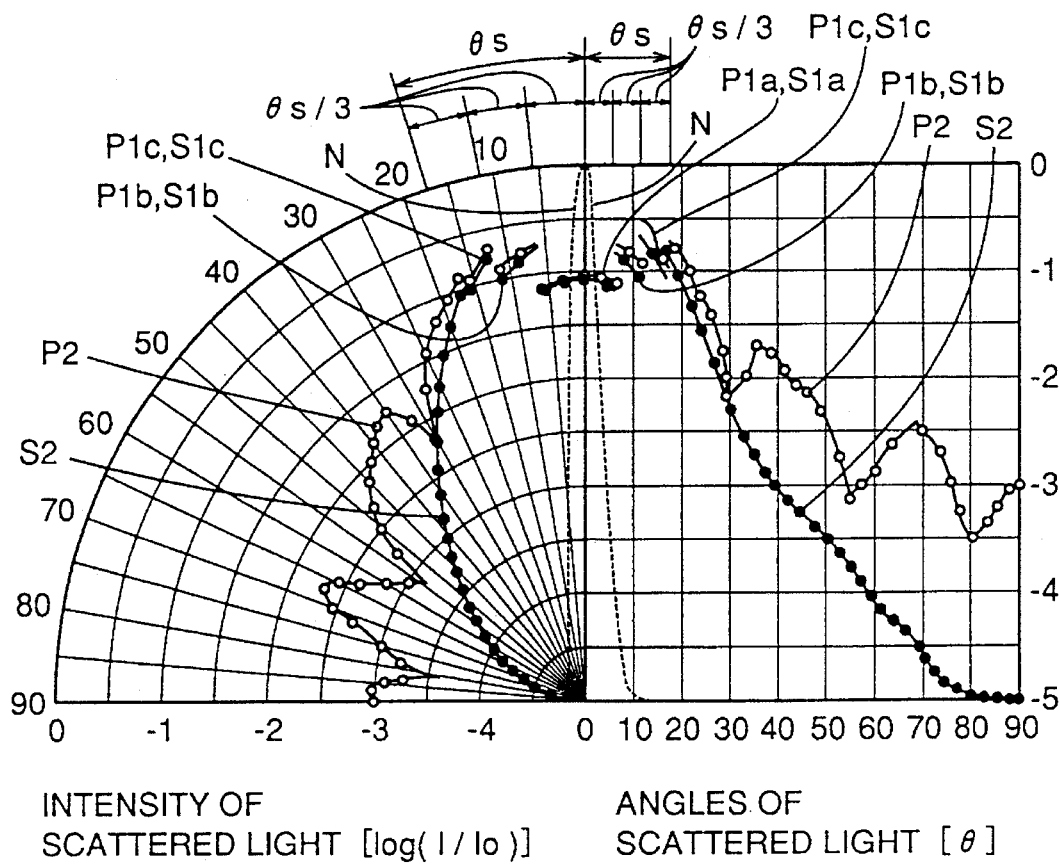
FIG. 9 is a graph showing measurement results of intensity of scattered light in the cases of the presence of particles, the presence of pits, and the absence of pits and particles on the surface of the sample, using the reflection adjustment portion and the light collecting portion according to the second embodiment as shown in FIGS. 6 and 7.

Referring to FIG. 9, the distribution of intensity of scattered light when there are particles on the sample measured by the semiconductor wafer inspection apparatus according to the second embodiment are represented by P1a, P1b, P1c, and P2. The distribution of intensity of scattered light when there are pits on the sample are represented by S1a, S1b, S1c, and S2. Distribution when there are neither pits nor particles on the surface of the sample is represented by N. In this second embodiment, the very fine adjustment of the distribution of intensity of scattered light within the range of scattering angles of $0-\theta_s$ can be realized by changing the reflectance of the reflection adjustment portions gradually in three steps. This, therefore, allows more correct detection of particles compared with the first embodiment shown in FIG. 3. Accordingly, measurement control portion 90 calculates the total amount of the intensity of scattered light with the change of the intensity of scattered light in the range of scattering angles of $0-\theta_s$ taken into consideration, resulting in improvement of accurate measurement of diameters and the number of particles.

Figure 10:
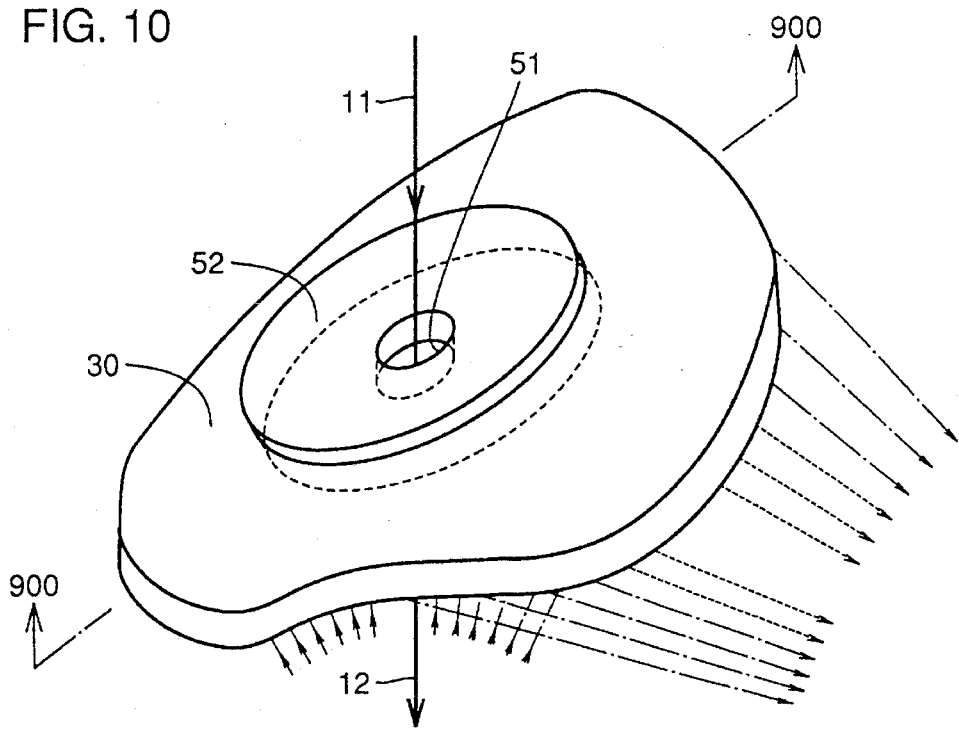
FIG. 10 is a oblique projection view showing a reflection adjustment portion and a light collection portion of a semiconductor wafer inspection apparatus according to a third embodiment of the present invention.
Figure 11:
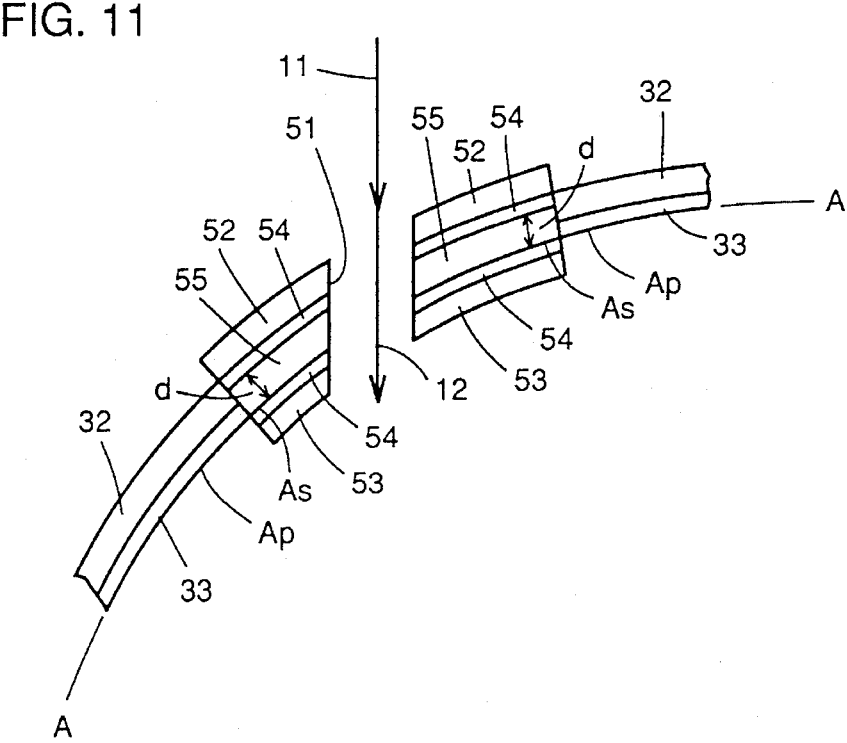
FIG. 11 is a sectional view of the reflection adjustment portion and the light collection portion according to the third embodiment taken along line 900—900 shown in FIG. 10.

A third embodiment is shown in FIGS. 10 and 11 in which a liquid crystal 55 having a dynamic scattering mode is used as the reflection adjustment portion. A transparent electrode 54 is formed to sandwich liquid crystal 55. A glass base material 52 of the reflection adjustment portion and a reflection adjustment glass material 53 are formed to sandwich transparent electrode 54.

Figure 12:
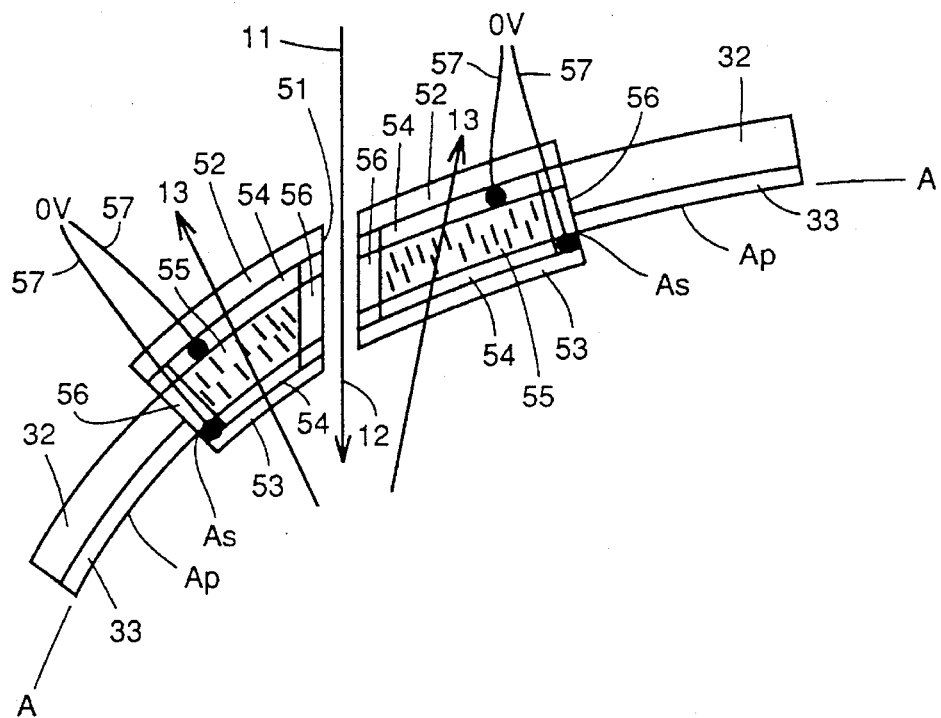
FIG. 12 is a sectional view showing in greater detail the reflection adjustment portion according to the third embodiment shown in FIG. 11.

Referring to FIG. 12 of the third embodiment, a liquid crystal sealing material 56 is arranged to seal liquid crystal 55. Lead lines 57, 57 are connected to transparent electrodes 54, 54, respectively, for applying a voltage to transparent electrodes 54. One lead line 57 is connected to transparent electrode 54 through liquid crystal sealing material 56.

Glass base material 52 of the reflection adjustment portion and reflection adjustment glass material 53 are made of inorganic or organic glass. Transparent electrode 54 is made of a transparent or semi-transparent conductive film such as a tin oxide film, an indium oxide film, or an evaporated-metal thin film. As liquid crystal 55, the liquid crystal having the dynamic scattering mode, such as MBBA (Methoxy Butyl Benzylidene Aniline) which is one of the liquid crystals in the nematic state is used. Liquid crystal sealing material 56 is made of a low melting point glass, an epoxy resin or the like. The surface of transparent electrode 54 is arranged such that longitudinal axes of molecules of liquid crystal 55 are oriented in a certain direction with respect to the surface of transparent electrode 54. Liquid crystal 55 is set to have a thickness d of about 8–about 60μm.

Now, referring to FIGS. 12 and 13, description will be made on an operation of the semiconductor wafer inspection apparatus according to the third embodiment.

As shown in FIG. 12, a voltage of 0 V is applied to transparent electrode 54 through lead line 57. Since molecules of liquid crystal 55 are arranged in one direction, most of the scattered light 13 passes through liquid crystal 55. Scattered light 13 then passes through glass base material 52 of the reflection adjustment portion. As a result, there is very little scattered light directed to the light receiving portion (not shown).

Figure 13:
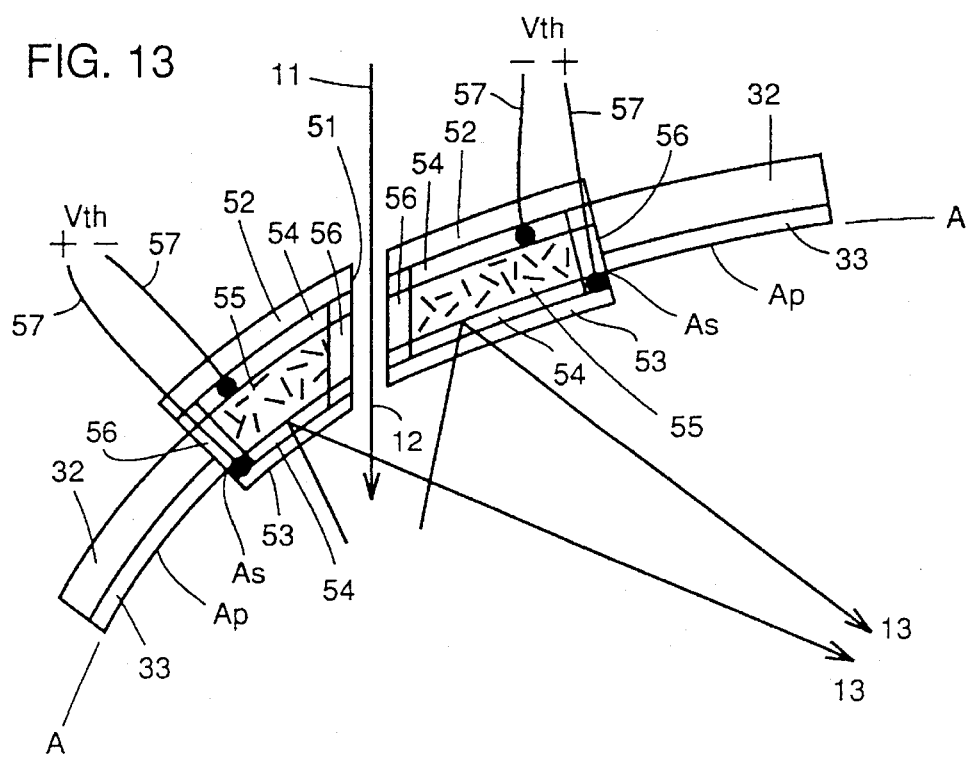
FIG. 13 is a sectional view showing an operation of the reflection adjustment portion according to the third embodiment shown in FIG. 12.

Next, as shown in FIG. 13, a voltage of at least $V_{th}$ which is a starting voltage value of the dynamic scattering mode (DSM) is applied to transparent electrode 54 through lead line 57. The applied voltage causes ions present in liquid crystal 55 to move, resulting in disarray of molecules of liquid crystal 55. Accordingly, light 13 is reflected from liquid crystal 55, and most of the scattered light is directed to the light receiving portion (not shown). If the voltage applied to liquid crystal 55 is $V_{th}$ or more, the reflectance of liquid crystal 55 increases as the applied voltage increases. Therefore, the reflectance of liquid crystal 55 can be changed easily by changing the voltage applied to liquid crystal 55.

Figure 14:
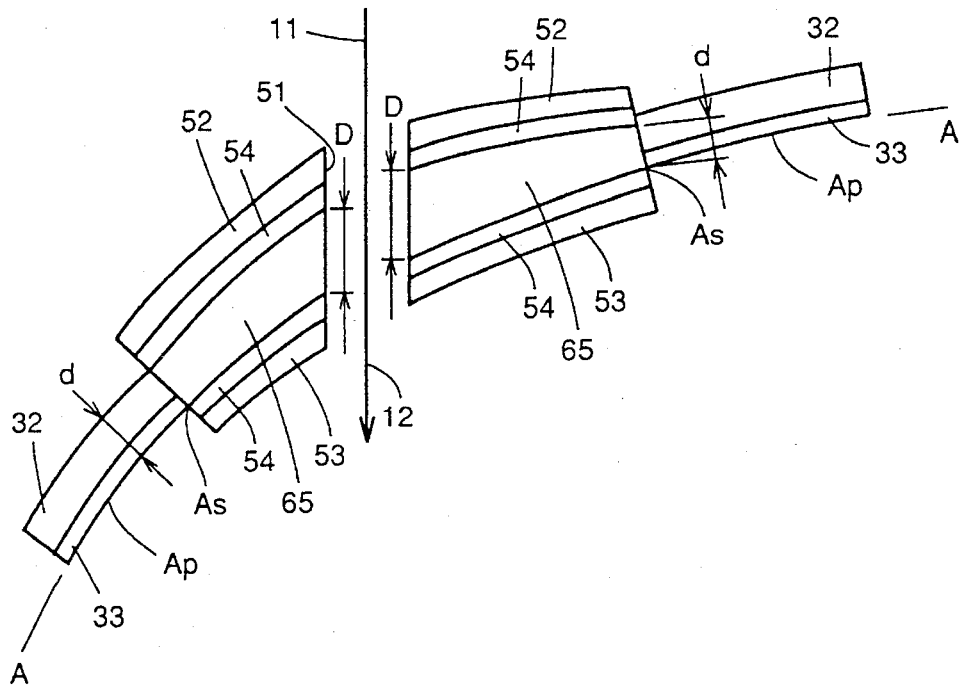
FIG. 14 is a sectional view showing a reflection adjustment portion and a light collecting portion of a semiconductor wafer inspection apparatus according to a fourth embodiment of the present invention.
Figure 15:
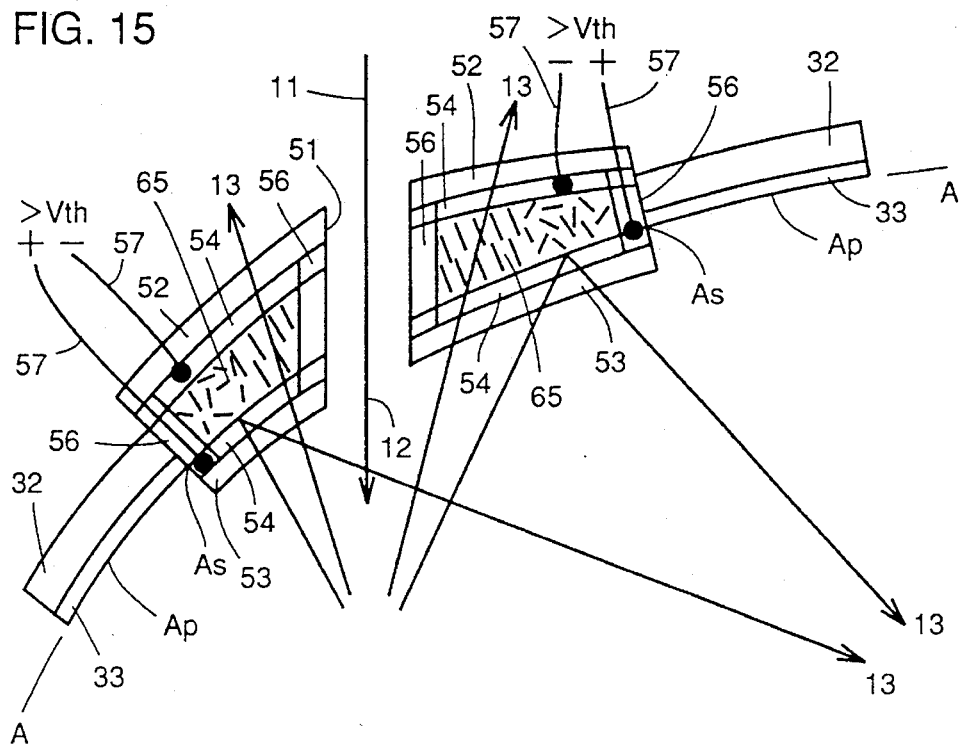
FIG. 15 is a sectional view showing an operation of the reflection adjustment portion according to the fourth embodiment shown in FIG. 14.

A fourth embodiment is shown in FIGS. 14 and 15 in which a thickness of a liquid crystal 65 is changed continuously compared with the third embodiment. More particularly, a thickness d on the side of base material 32 of the light collecting portion of liquid crystal 65 is set to, for example, 8–10μm, and a thickness D on the side of optical beam inlet hole 51 of liquid crystal 65 is set to 50–60μm. Changing the thickness of liquid crystal 65 continuously as above, the light reflectance of liquid crystal 65 can be changed continuously. In other words, in this fourth embodiment, if the voltage applied to liquid crystal 65 is less than $V_{th}$ which represents the starting voltage of the dynamic scattering mode, most of the scattered light passes through liquid crystal 65. As the voltage applied to liquid crystal 65 is made larger to exceed the starting voltage of $V_{th}$, the dynamic scattering mode starts from the thin base material 32 side of the light collecting portion (see FIG. 15). As the applied voltage is further increased, the dynamic scattering mode spreads to the side of optical beam inlet hole 51. When the applied voltage becomes $V_{th} \times (D/d)$ or more, the dynamic scattering mode can be seen in the entire liquid crystal 65. In those portions where the dynamic scattering mode has already started, the disorder of molecule arrangement of liquid crystal 65 becomes more apparent according to the increase of the applied voltage, resulting in a still larger reflectance in those portions.

In this fourth embodiment, therefore, the reflectance of the reflection adjustment portion within the range of scattering of angles $0-\theta_s$ can be changed continuously and gradually from the base material 32 side of the light collecting portion, compared with the third embodiment. This allows very fine adjustment of the distribution of the intensity of scattered light. As a result, the distribution of the intensity of scattered light can be adjusted easily so as to optimize the signal-to-noise ratio.

Figure 16:
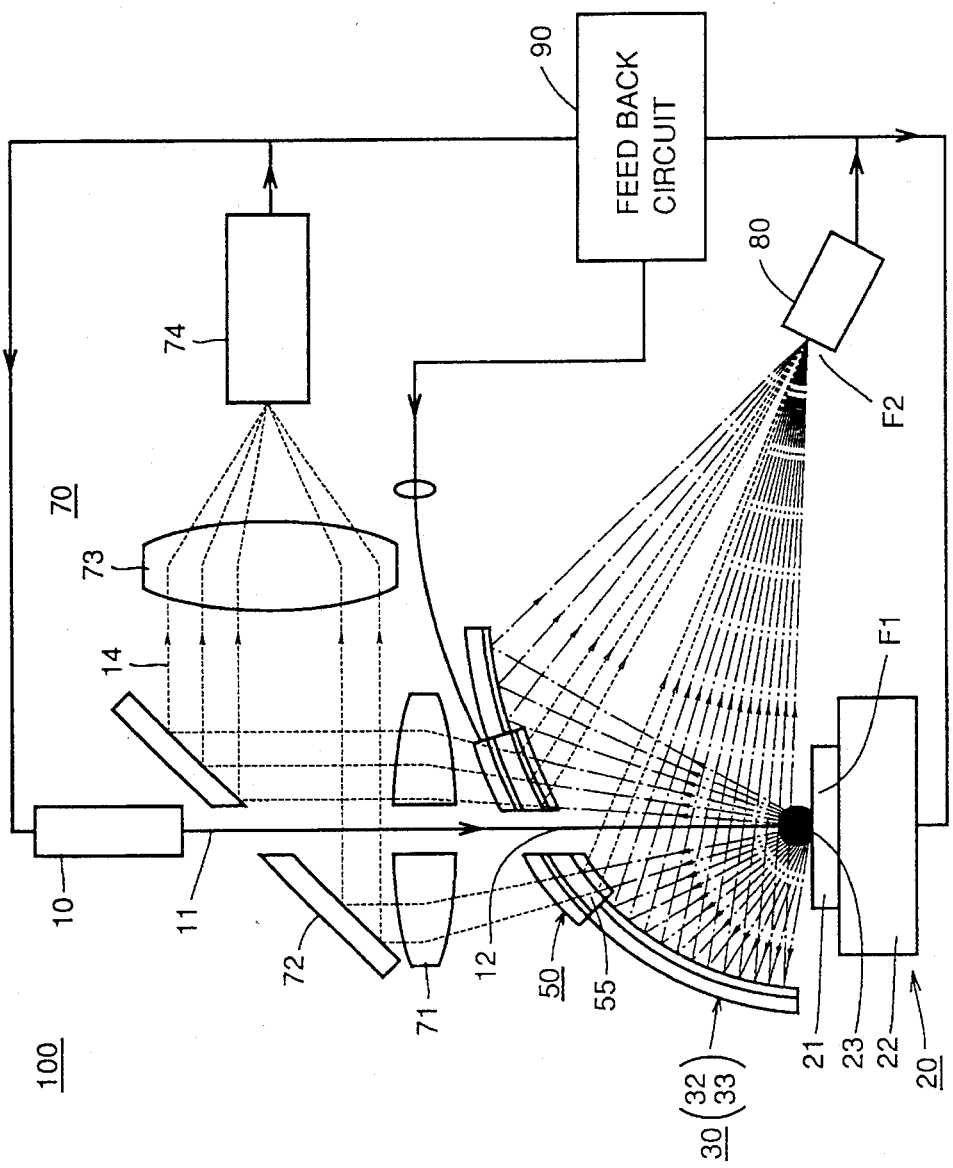
FIG. 16 is a schematic diagram showing a structure of a semiconductor wafer inspection apparatus according to a fifth embodiment of the present invention.
Figure 17:
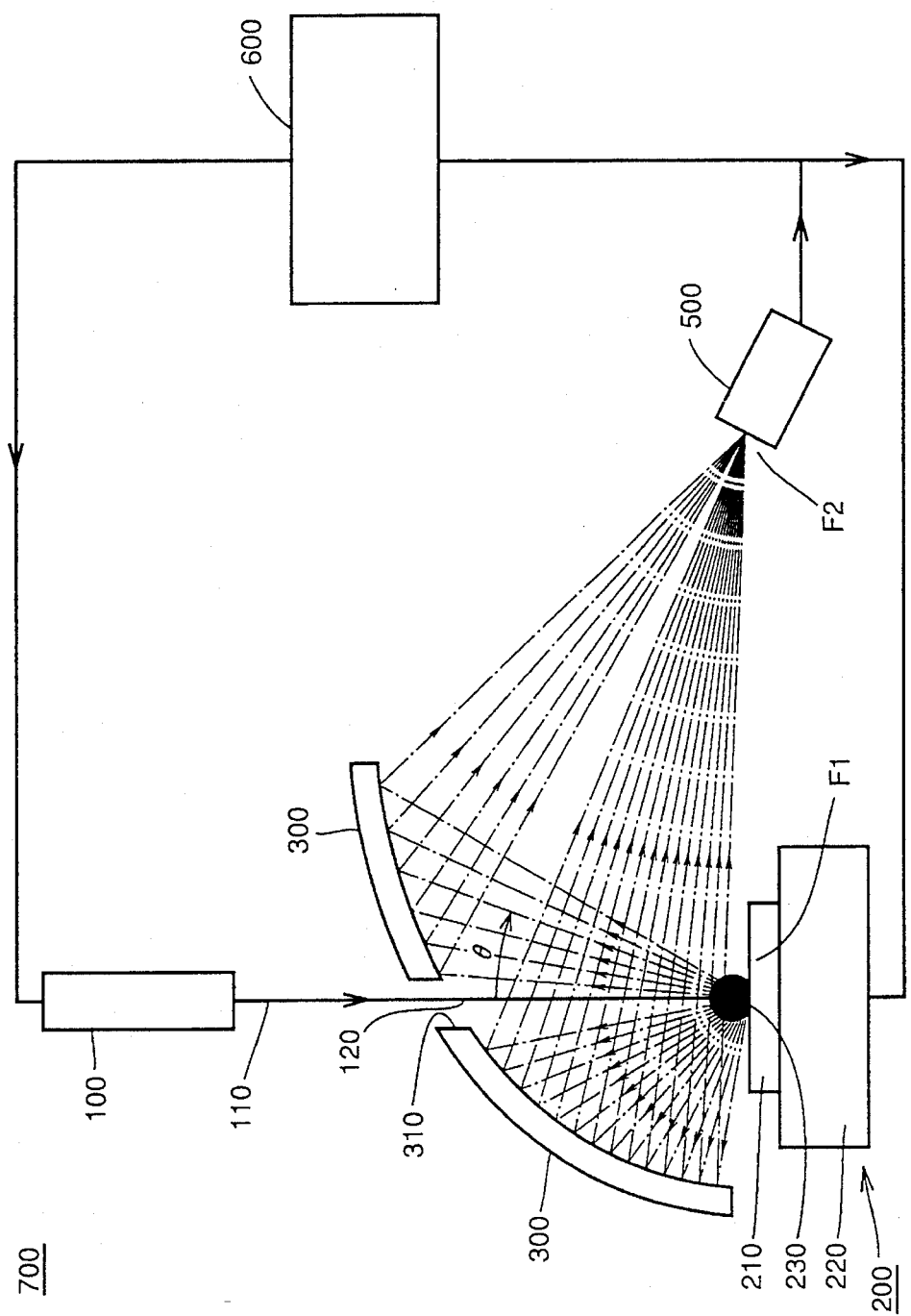
FIG. 17 is a schematic diagram showing a structure of a conventional semiconductor wafer inspection apparatus.
Figure 18:
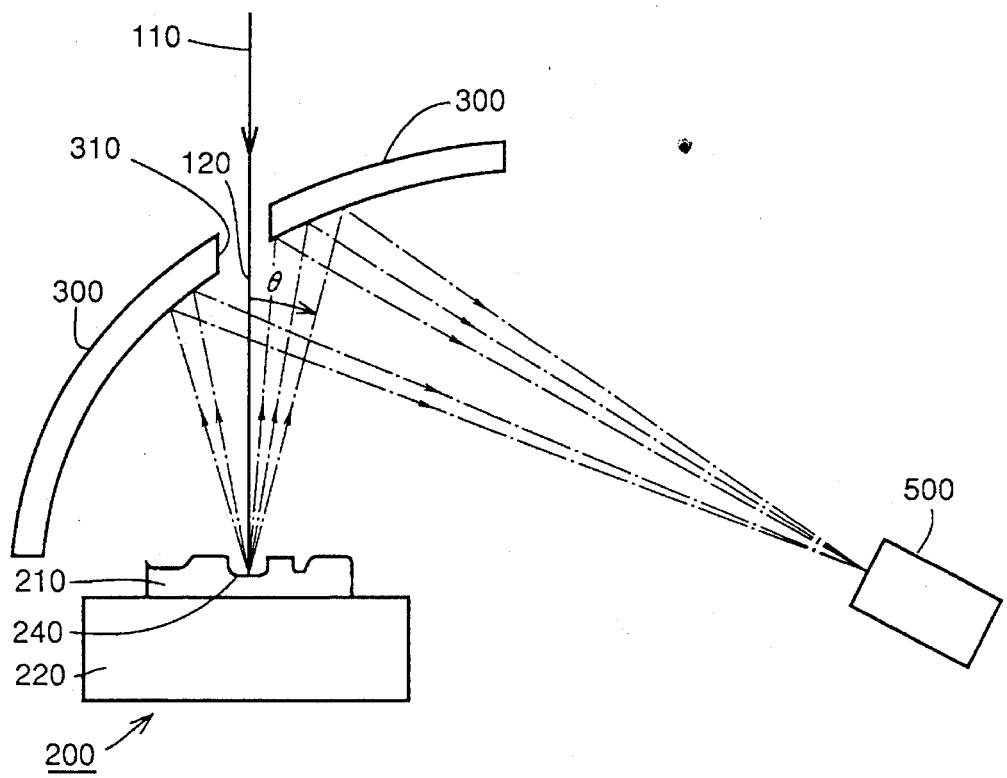
FIG. 18 is a schematic diagram showing scattering light when pits on the surface of the sample are detected by the conventional semiconductor wafer inspection apparatus shown in FIG. 17.
Figure 19:
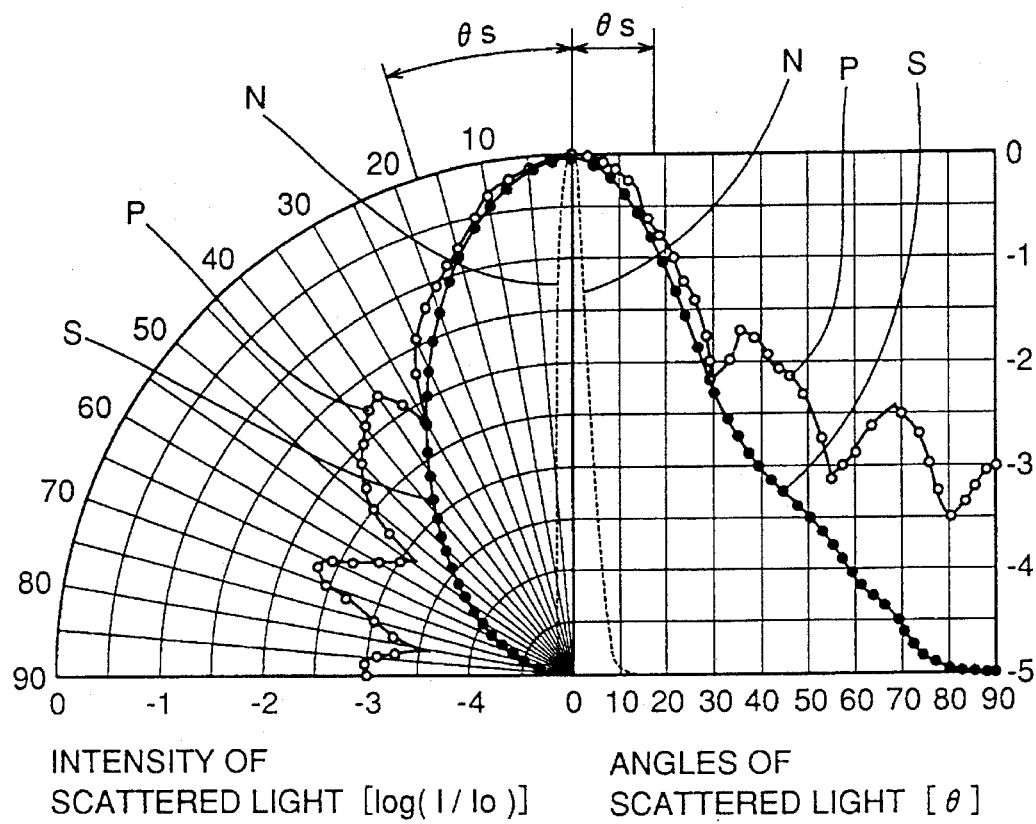
FIG. 19 is a graph showing measurement results of intensity of scattered light in the cases of the presence of particles, the presence of pits, and the absence of pits and particles on the surface of the sample, using the conventional semiconductor wafer inspection apparatus as shown in FIG. 17.

A semiconductor wafer inspection apparatus according to the fifth embodiment is shown in FIG. 16 in which reflection adjustment portion 50 is similar to that of the third embodiment shown in FIG. 11. In this fifth embodiment, a reference light portion 70 is provided for detecting a reference light transmitted through reflection adjustment portion 50. Reference light portion 70 includes a collimator lens 71, a reflection mirror 72, a light condenser lens 73, and an optical detector 74.

Now, an operation of the semiconductor wafer inspection apparatus according to the fifth embodiment will be described below.

Among the scattered light, a reference light 14 transmitted through liquid crystal 55 passes through collimater lens 71. Reflection mirror 72 changes the light path of reference light 14. Then, reference light 14 is projected to light detector 74 from light collecting lens 73. Optical detector 74 is made of, for example, a photomultiplier.

Reference light 14 reflected at an average reflectance of reflection adjustment portion 50 is photoelectrically converted to an output signal by optical detector 74. Optical detector 74 sends the output signal to a feedback circuit (not shown) in measurement control portion 90. The feedback circuit sets an applied voltage which provides the average reflectance of reflection adjustment portion 50 of a predetermined value. The set voltage is applied to transparent electrode 54 in reflection adjustment portion 50.

As described above, the fifth embodiment realizes control of the average reflectance of reflection adjustment portion 50 correctly to the predetermined value by using the feedback circuit. Such an average reflectance of reflection adjustment portion 50 can be changed easily by changing the set value of the feedback circuit.

In the first through fifth embodiments, the reflectance of the reflection adjustment portion is made smaller than that of the light collecting portion. However, the present invention is not limited thereto and instead the reflectance of the reflection adjustment portion may be made larger than the reflectance of the light collecting portion. In this case, measurements are made mainly in the range of scattering angles where intensity of scattered light is large, so that abnormal conditions on the surface of the sample such as the presence of pits and particles can be detected with high sensitivity.

As described above, in a semiconductor wafer inspection apparatus according to the present invention, a light collecting means includes a light collecting portion having a first light reflectance and a reflection adjustment portion having a second light reflectance different from the first light reflectance, so that, for example, if the second light reflectance is made smaller than the first light reflectance, an intensity of light emitted from the reflection adjustment portion becomes smaller than that emitted from the light collecting portion even though an intensity of light entered the light collecting portion is equal to that entered the reflection adjustment portion. By adopting such a reflection adjustment portion within the range of scattering angles where the same distribution of intensity of scattered light is provided when there are particles and when there are pits on the surface of a sample, the intensity of scattered light within the range of those scattering angles is relatively reduced compared with the intensity of scattered light in the range of other scattering angles. As a result, the intensity of scattering in the range of scattering angles where the difference between the intensity of scattered light caused by particles and that caused by pits is apparent can be increased relatively. Ratio of a total amount of scattered light caused by particles to that caused by pits can thus be emphasized than before. This allows easy and clear distinguishment of the scattered light caused by pits from the scattered light caused by particles, eliminating an inconvenience such as an erroneous identification of the scattered light caused by pits as that caused by particles as before. On the other hand, even in the range of scattering angles where the intensity of scattering is reduced by the reflection adjustment portion, the intensity of scattering is held at a certain level, so that the presence of particles can easily be detected. Therefore, diameters and the number of particles on the surface of the sample can be detected correctly. If the second light reflectance is made larger than the first reflectance, and the reflection adjustment portion is installed in the range of scattering angles where the intensity of scattered light is large, then anything abnormal on the surface of the sample can be detected with high sensitivity. Further, if the reflection adjustment portion is made to include a first reflection adjustment portion having a third light reflectance and a second reflection adjustment portion having a fourth light reflectance different from the third light reflectance, the distribution of intensity of scattered light reflected from the reflection adjustment portion can be adjusted more properly. Further, if the reflection adjustment portion is made to include a liquid crystal having a dynamic scattering mode, the reflectance of the reflection adjustment portion can be easily changed by changing a voltage value applied to the liquid crystal.

In another semiconductor wafer inspection apparatus of the present invention, a light collecting means is made to include a reflection adjustment portion made of a liquid crystal and having a second light reflectance, a reference light detecting means detects a reference light transmitted through the liquid crystal of the reflection adjustment portion, and light reflectance control means controls the light reflectance of the reflection adjustment portion based on a detection output of the reference by detecting means. Therefore, the dynamic scattering mode of the liquid crystal can be controlled easily in a feedback loop by the reference light reflected at the reflectance of the reflection adjustment portion. The light reflectance of the reflection adjustment portion can thus be controlled correctly to a predetermined value.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A semiconductor wafer inspection apparatus comprising:

light projecting means for directing a beam of light to a main surface of a semiconductor wafer;

light collecting means for collecting beams of light scattered from the main surface of said semiconductor wafer; and light receiving means receiving the scattered light collected by said light collecting means for measuring intensity of the scattered light; wherein said light collecting means includes
a light collecting portion having a first light reflectance, and
a reflection adjustment portion having a second light reflectance different from said first light reflectance.

2. The semiconductor wafer inspection apparatus according to claim 1, wherein said second light reflectance is smaller than said first light reflectance.

3. The semiconductor wafer inspection apparatus according to claim 1, wherein said reflection adjustment portion includes
a first reflection adjustment portion having a third light reflectance, and
a second reflection adjustment portion having a fourth light reflectance different from said third light reflectance.

4. The semiconductor wafer inspection apparatus according to claim 3, wherein said first reflection adjustment portion and said second reflection adjustment portion both include a stepped portion.

5. The semiconductor wafer inspection apparatus according to claim 1, wherein said reflection adjustment portion includes a liquid crystal having a dynamic scattering mode.

6. The semiconductor wafer inspection apparatus according to claim 5, wherein said liquid crystal has a thickness which changes continuously in accordance with an angle of light scattering.

7. The semiconductor wafer inspection apparatus according to claim 1, wherein said reflection adjustment portion is set in such a scattering angle range that the scattered light having a large intensity of scattering enters.

8. The semiconductor wafer inspection apparatus according to claim 1, wherein said light collecting portion and said reflection adjustment portion has the same ellipsoid of revolution.

9. The semiconductor wafer inspection apparatus according to claim 1, wherein said light collecting portion includes a base material of the light collecting portion and a light collecting film, and wherein said reflection adjustment portion includes a base material of the reflection adjustment portion and a reflection adjustment film.

10. A semiconductor wafer inspection apparatus comprising:

light projecting means for directing a beam of light to a main surface of a semiconductor wafer;

light collecting means including a light collecting portion having a first light reflectance and a reflection adjustment portion made of a liquid crystal having a second light reflectance different from said first light reflectance, for collecting beams of light scattered from the main surface of said semiconductor wafer;

light receiving means receiving the scattered light collected by said light collecting means for measuring intensity of said scattered light;

reference light detecting means for detecting a reference light transmitted through the liquid crystal of said reflection adjustment portion; and light reflectance control means for controlling the light reflectance of said reflection adjustment portion according to a detection output of said reference light detecting means.

11. A semiconductor wafer inspection apparatus according to claim 10, wherein said reference light detecting means includes a light collecting lens and an optical detector.

* * * * *